(12) United States Patent
Esenaliev et al.

(10) Patent No.: US 12,702,306 B2
(45) Date of Patent: Aug. 11, 2026

(54) USING AN OPTICAL ENERGY METER TO NORMALIZE ACOUSTIC SIGNALS GENERATED BY LASER PULSES OF VARIOUS WAVELENGTHS TO PERMIT ACCURATE CALCULATION OF BLOOD OXYGENATION

(71) Applicants: Noninvasix, Inc., Galveston, TX (US); The Board of Regents of The University of Texas System, Austin, TX (US)

(72) Inventors: Rinat Esenaliev, League City, TX (US); Irene Petrov, Galveston, TX (US); Yuriy Petrov, Galveston, TX (US)

(73) Assignees: Noninvasix, Inc., Galveston, TX (US); The Board of Regents of The University of Texas System, Austin, TX (US)

( * ) Notice: Subject to any disclaimer, the term of this patent is extended or adjusted under 35 U.S.C. 154(b) by 471 days.

(21) Appl. No.: 18/187,614

(22) Filed: Mar. 21, 2023

(65) Prior Publication Data

US 2023/0233088 A1 Jul. 27, 2023

Related U.S. Application Data

(63) Continuation of application No. PCT/US2021/051608, filed on Sep. 22, 2021.

(Continued)

(51) Int. Cl.
*A61B 5/1455* (2006.01)
*A61B 5/00* (2006.01)

(52) U.S. Cl.
CPC ........ *A61B 5/0095* (2013.01); *A61B 5/14551* (2013.01); *A61B 2562/0204* (2013.01)

(58) Field of Classification Search
CPC .................................................... A61B 5/1455
See application file for complete search history.

(56) References Cited

U.S. PATENT DOCUMENTS 6,309,352 B1 10/2001 Oraevsky et al.
6,498,942 B1 12/2002 Esenaliev et al.

(Continued)

FOREIGN PATENT DOCUMENTS

JP 2010088627 A 4/2010
JP 2015501175 A 1/2015

(Continued)

OTHER PUBLICATIONS

PCT/US21/51608 International Search Report and Written Opinion dated Dec. 10, 2021.

(Continued)

*Primary Examiner* — Marjan Fardanesh
(74) *Attorney, Agent, or Firm* — Wilson Sonsini Goodrich & Rosati

(57) ABSTRACT

The systems, devices, and methods herein make optoacoustic measurements and correct or normalize them for variations in optical energy level of the different light pulses used. An optical source directs optical pulses to tissue, an optical energy meter measures the optical energy of the different optical pulses, an acoustic detector measures an acoustic response generated by the tissue in response to the optical pulses, and a processor calculates a concentration of an analyte based on the measured acoustic response and as corrected or normalized for the different energy levels among the optical pulses.

22 Claims, 3 Drawing Sheets

Related U.S. Application Data

(60) Provisional application No. 63/084,706, filed on Sep. 29, 2020.

(56) References Cited

U.S. PATENT DOCUMENTS

| | | | |
|---|---|---|---|
| 6,751,490 | B2 | 6/2004 | Esenaliev et al. |
| 7,430,445 | B2 | 9/2008 | Esenaliev et al. |
| 8,352,005 | B2 | 1/2013 | Esenaliev et al. |
| 9,380,967 | B2 | 7/2016 | Esenaliev et al. |
| 10,226,206 | B2 | 3/2019 | Esenaliev et al. |
| 10,231,656 | B2 | 3/2019 | Esenaliev et al. |
| 10,307,088 | B2 | 6/2019 | Esenaliev et al. |
| 11,045,121 | B2 | 6/2021 | Esenaliev et al. |
| 11,109,782 | B2 | 9/2021 | Esenaliev et al. |
| 2003/0010898 | A1 | 1/2003 | Mackenzie et al. |
| 2004/0054268 | A1 | 3/2004 | Esenaliev et al. |
| 2008/0255433 | A1 | 10/2008 | Prough et al. |
| 2014/0049770 | A1 | 2/2014 | Li et al. |
| 2016/0262674 | A1 | 9/2016 | Esenaliev et al. |
| 2017/0042429 | A1 | 2/2017 | Nakajima |
| 2019/0231239 | A1 | 8/2019 | Prough et al. |

FOREIGN PATENT DOCUMENTS

| | | | |
|---|---|---|---|
| WO | WO-2004010866 | A1 | 2/2004 |
| WO | WO-2004096082 | A2 | 11/2004 |
| WO | WO-2013056089 | A2 | 4/2013 |
| WO | WO-2014144301 | A1 | 9/2014 |
| WO | WO-2016007678 | A1 | 1/2016 |
| WO | WO-2016149107 | A1 | 9/2016 |
| WO | WO-2018049415 | A1 | 3/2018 |
| WO | WO-2019170716 | A1 | 9/2019 |

OTHER PUBLICATIONS

Prahl, Scott. Optical Absorption of Hemoglobin. 1999. https://omlc.org/spectra/hemoglobin/.

JP2023-518833 Office Action dated Dec. 25, 2024, and an English translation.

USING AN OPTICAL ENERGY METER TO NORMALIZE ACOUSTIC SIGNALS GENERATED BY LASER PULSES OF VARIOUS WAVELENGTHS TO PERMIT ACCURATE CALCULATION OF BLOOD OXYGENATION

CROSS-REFERENCE

This application is a continuation of PCT Application No. PCT/US21/51608, filed Sep. 22, 2021; which claims priority to U.S. Provisional Application No. 63/084,706, filed Sep. 29, 2020; which application is fully incorporated herein by reference.

BACKGROUND

The present disclosure relates to medical systems, devices, and methods, particularly for measuring concentrations of analytes in tissue, such as for determining blood oxygenation and/or hemoglobin concentration.

Many research, medical, and clinical applications require the measurement of concentration of an analyte. Pulse oximetry, for example, is a commonly used technique to determine a subject's blood oxygenation in real-time. Pulse oximetry, however, faces many challenges in determining blood oxygenation in deeper blood vessels which can give a better indication of the overall levels of the subject's blood oxygenation. Hence, alternative techniques such as optoacoustic or photoacoustic measurements have been developed. Nevertheless, improvements to optoacoustic or photoacoustic measurement technology, for example, to improve measurement accuracy, are desired.

SUMMARY

The present disclosure relates generally to medical systems, devices, and methods for their use, and particularly photoacoustic or optoacoustic measurement and diagnostic systems, devices, and methods. Systems, devices, and methods to determine one or more physiological parameters optoacoustically (i.e., photoacoutically) are described. Systems, devices, and methods to correct such optoacoustic measurements based on the measured optical energy levels of the plurality of light pulses used to interrogate the sample are described.

One or more optical sources of an exemplary system may direct a plurality of optical pulses to tissue such as skin. An acoustic detector of the system may detect the acoustic response generated by the tissue in response to the optical pulses. Calculations of analyte concentration can be based on various characteristics and/or ratios between various characteristics, for example, the amplitude(s) of the acoustic signal(s) that are generated in the tissue in response to the optical pulses. Because of signal averaging, each calculation may depend on the ratios between groups of optical pulses at each of multiple wavelengths. Variations in the amplitude of optical energy generated by optical sources at each wavelength can result in inaccurate calculations of analyte concentration. Exemplary systems of the present disclose may further include an optical energy meter to measure optical energy levels of the optical pulses directed to the tissue. A processor of the system may calculate the concentration of the analyte, typically hemoglobin, based on the acoustic responses as normalized or corrected for different energy levels of the different light pulses that lead to the acoustic responses. More accurate optoacoustic measurements and analyte concentration calculations can then be made by applying such correction or normalization for the acoustic responses. In particular, optical energy at each wavelength can be measured with the energy meter and the resulting acoustic signal(s) can be normalized to a predetermined energy level(s).

The energy of every pulse emitted by the light source may be measured very close to the output orifice of the light source, for example, by directing part of the energy of a pulse into the aperture of the optical energy meter, such as with a beam splitter. The rest of the energy of the pulse may be directed to the tissue through a light-delivery system which may include one or more optical fibers or light guides. The processor can be instructed to divide the waveform of the acoustic signal generated in response to the light pulse by the energy of the light pulse, thereby normalizing the waveform of the acoustic signal.

In many embodiments, light pulses at different wavelengths are used. When several wavelengths are used, as the transmission of light-delivery system can differ at different wavelengths, the ratio of energy measured by energy meter at the light source output and energy incident on the tissue after passing through the light-delivery system may be established in advance for each of the used wavelengths in a system calibration step or steps. The processor can be instructed to use calibration coefficients when normalizing the acoustic signal for its energy and optionally apply additional multiplier(s) or divider(s), depending on the chosen ratio type.

Aspects of the present disclosure provide methods of measuring a concentration of an analyte. An exemplary method may comprise steps of: directing a plurality of optical pulses to tissue; measuring optical energy levels of the plurality of optical pulses directed to the tissue; measuring a plurality of acoustic responses of the tissue in response to the plurality of optical pulses directed to the tissue; normalizing the plurality of measured acoustic responses based on the measured optical energy levels; and, determining a concentration of an analyte based on the plurality of normalized acoustic responses.

In some embodiments, the step of directing the plurality of optical pulses to the tissue comprises steps of directing a first optical pulse at a first wavelength to the tissue and directing a second optical pulse at a second wavelength to the tissue, wherein the first and second wavelengths are different.

In some embodiments, the plurality of optical pulses is at one or more wavelengths from 600 nm to 1,300 nm.

In some embodiments, the plurality of acoustic responses of the tissue are measured from a same side of the tissue the plurality of optical pulses is directed from.

In some embodiments, the plurality of acoustic responses of the tissue are measured from a different side of the tissue the plurality of optical pulses is directed from.

In some embodiments, the analyte is one or more of hemoglobin, oxyhemoglobin, and deoxyhemoglobin.

In some embodiments, the method may further comprise a step of determining blood oxygenation based on the determined concentration of one or more analytes and the characterized property of the tissue.

In some embodiments, the tissue comprises one or more blood vessels and tissue surrounding the one or more blood vessels.

Aspects of the present disclosure provide systems for measuring a concentration of an analyte. An exemplary system may comprise: at least one optical source to direct a plurality of optical pulses to tissue; an optical energy meter to measure optical energy levels of the plurality of optical pulses directed to the tissue; an acoustic detector to measure a plurality of acoustic responses of the tissue to the plurality of optical pulses; and, a processor to normalize the plurality of measured acoustic responses based on the measured optical energy levels and determine a concentration of an analyte based on the plurality of normalized acoustic responses.

In some embodiments, the plurality of optical sources comprises a first optical source configured to generate a first optical pulse at a first wavelength and a second optical source configured to generate a second optical pulse at a second wavelength, wherein the first and second wavelengths are different.

In some embodiments, the plurality of optical pulses is at one or more wavelengths from 600 nm to 1,300 nm.

In some embodiments, the at least one optical source comprises a plurality of optical sources, each optical source configured to generate an optical pulse at a different wavelength.

In some embodiments, the at least one optical source and the acoustic detector are oriented on a same side as one another with respect to the tissue.

In some embodiments, the at least one optical source and the acoustic detector are oriented on different sides of one another with respect to the tissue.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings. Matching reference numerals designate corresponding parts throughout the figures, which are not necessarily drawn to scale.

DETAILED DESCRIPTION

Reference will now be made in detail to various embodiments, examples of which are illustrated in the accompanying drawings. In the following detailed description, numerous specific details are set forth in order to provide a thorough understanding of the invention(s) of the present disclosure and the described embodiments. However, the invention is optionally practiced without these specific details. In other instances, well-known methods, procedures, components, and circuits have not been described in detail so as not to unnecessarily obscure aspects of the embodiments.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

Figure 1A:
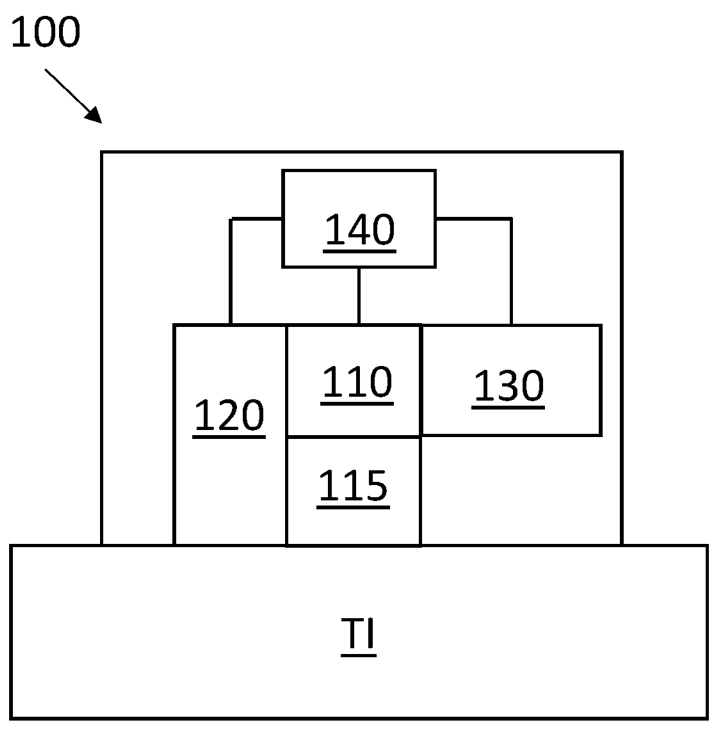
FIG. 1A shows a schematic of an optoacoustic measurement system operating in a reflection mode, according to embodiments of the present disclosure.
Figure 1B:
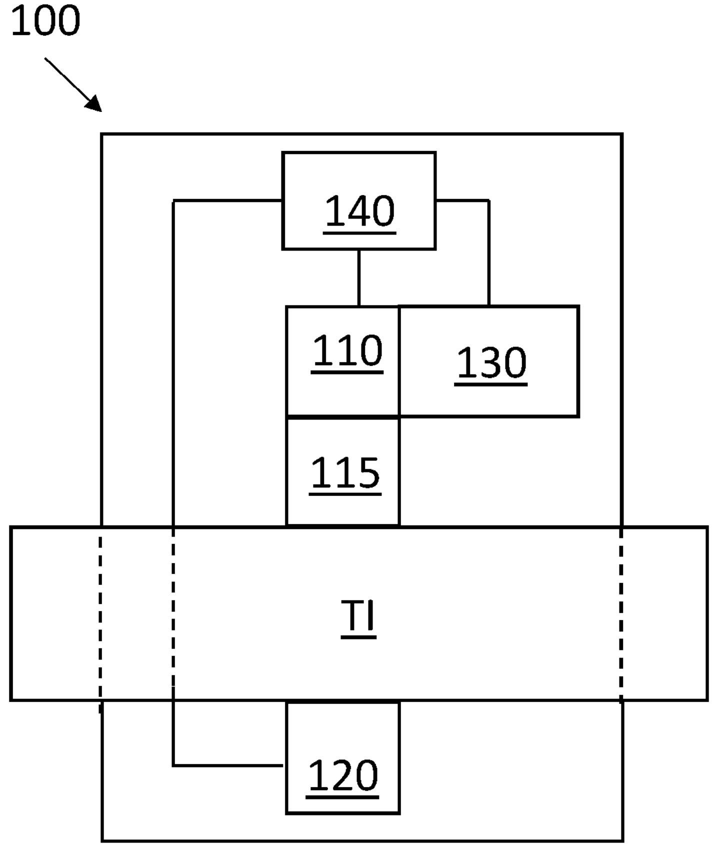
FIG. 1B shows a schematic of an optoacoustic measurement system operating in a transmission mode, according to embodiments of the present disclosure.

FIGS. 1A and 1B show an exemplary optoacoustic measurement system 100. The optoacoustic measurement system 100 may comprise a light or optical source 110 for generating one or more light or optical pulses, an acoustic sensor 120, an optical energy sensor 130 operatively coupled to the light or optical source 110, a light-delivery system 115 coupled to the light or optical source 110, and a processor 140 operatively coupled to the light or optical source 110, the acoustic sensor 120, and the optical energy sensor 130. The optical energy sensor 130 may be, for example, a DET 100A detector from Thorlabs of Newton, New Jersey, a PE25-C or PE50BB-DIF-C detector from Ophir Optics of Jerusalem, Israel, or an EnergyMax sensor from Coherent Inc. of Santa Clara, California. The light or optical source 110 may be an optical parametric oscillator (OPO), a light-emitting diode (LED), laser diode, laser diode array, other pulsed light source with pulses of nanosecond duration, or the like to name a few examples. The light or optical source 110 may be coupled to the light delivery system 115 which may be oriented to direct one or more light pulses to the tissue TI, such as skin or other superficial tissue. Examples of suitable tissue TI to be interrogated include superficial veins on an infant's hand or an adult's finger, radial artery, superior sagittal sinus, internal jugular vein, and other blood vessels. The one or more light pulses may be short, typically shorter than one hundred nanoseconds, pulses of near-infrared (NIR) light at a wavelength to be absorbed by a chromophore, e.g., hemoglobin. The one or more light pulses may be at wavelengths in the visible, infrared, and/or ultraviolet ranges, for example, at wavelength range of 600 nm to 1,300 nm, such as 805 nm, the isobestic point of hemoglobin. The light pulse(s) may have a wide range of energy levels, as limited by light source or laser, tissue safety, patient safety, and other considerations, for example, an energy level of between 1 μJ to 1 mJ. The light pulse(s)

may have a wide range of repetition rates, for example, repetition rate between 1 to 10,000 Hz.

The acoustic sensor 120 may be configured to detect acoustic signal(s) generated by the tissue TI in response to the one or more light pulses directed to the tissue TI. The acoustic sensor 120 may be configured to operate in a reflection mode whereby the acoustic sensor 120 is oriented on the same side relative to the tissue TI as the optical source 110 and can detect the acoustic signal(s) at that location, as shown in FIG. 1A. Alternatively or in combination, the acoustic sensor 120 may be configured to operate in a transmission mode whereby the acoustic sensor 120 is oriented on the opposite side relative to the tissue TI as the optical source 110 and can detect the acoustic signal(s) at that location, as shown in FIG. 1B. The acoustic sensor 120 may comprise a single wide-band acoustic detector, an acoustic array, or an acoustic matrix, to name a few examples. The system and one or more components such as the acoustic sensor 120 operating in a reflection mode can be used to interrogate any superficial vein or blood vessel because total tissue thickness may not be a limiting factor.

The processor 140 may be operatively coupled to the acoustic sensor 120 and the optical energy sensor 130 to normalize detected acoustic responses based on the different optical intensities detected. For example, a first acoustic response from the tissue TI in response to a first optical pulse with a first optical energy may be detected, a second acoustic response from the tissue TI in response to a second optical pulse with a different second optical energy may be detected, and so forth, and the different acoustic responses may be normalized for the different optical energies. Based on the normalized acoustic response values, the processor 130 may calculate a concentration of an analyte, such as total hemoglobin (THb), oxyhemoglobin, and deoxyhemoglobin, to name a few examples. The calculated concentration may be displayed or otherwise provided to the user with a user interface of the system 100, such as a visual display.

Figure 2:
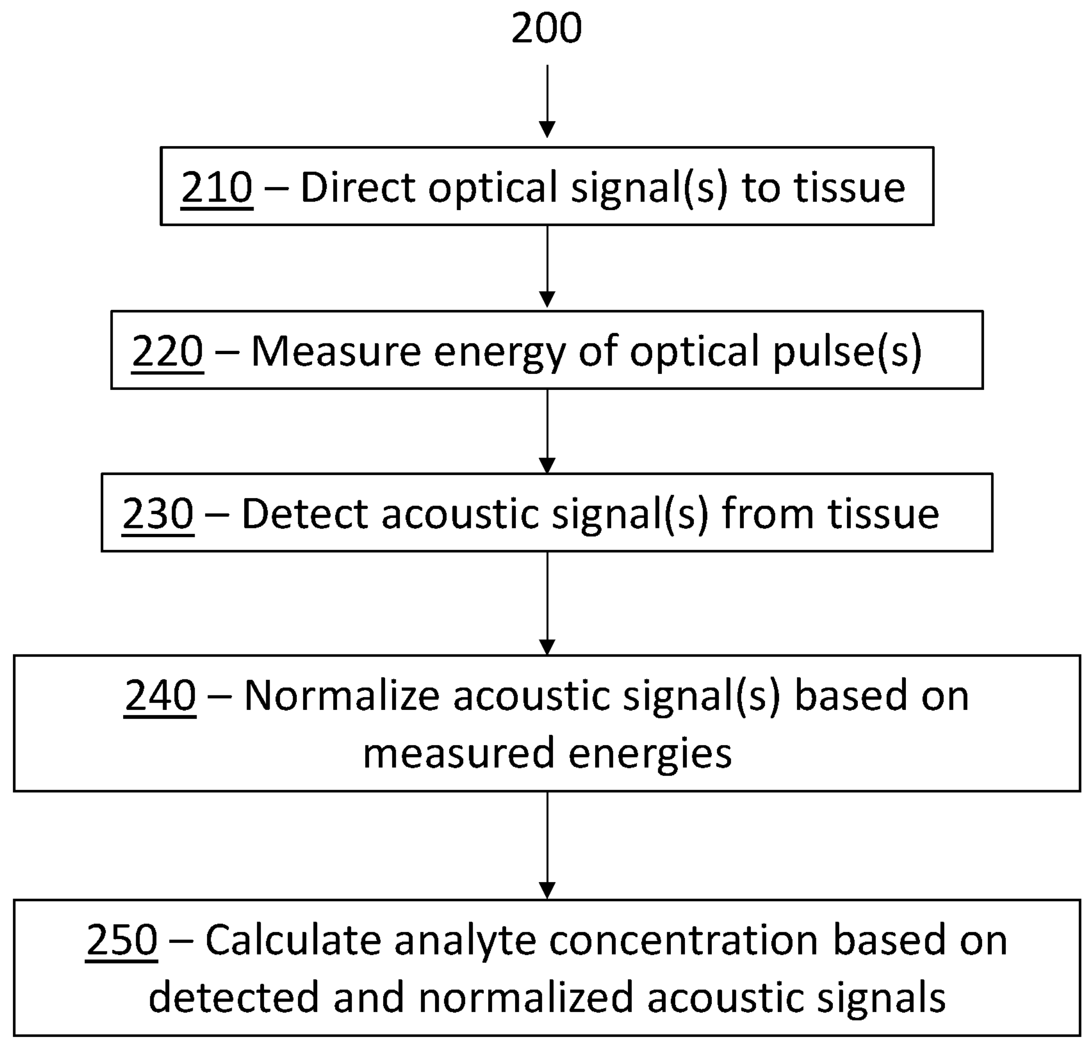
FIG. 2 shows a flow chart of an exemplary method of optoacoustic measurement, according to embodiments of the present disclosure.

FIG. 2 shows a flow chart of an exemplary method 200 of optoacoustic measurement. In a step 210, one or more optical pulses are directed to tissue such as skin or other superficial tissue. The one or more light pulses may be at the wavelength ranges, the energy level ranges, and/or the repetition rate ranges described herein. Typically, a plurality of optical pulses each at different wavelengths are directed to the tissue. In embodiments where a plurality of optical pulses is directed to the tissue, each optical pulse may be at different wavelengths. In a step 220, the optical energies of the optical pulse(s) are measured with an optical energy meter. In a step 230, the acoustic signal generated in response to the one or more optical pulses may be detected. In a step 240, the acoustic signals may be normalized based on the measured optical energies. The acoustic signals in response to the different light or optical pulses may be normalized to correct for the different energies of the light or optical pulses. In a step 250, the analyte concentration may be calculated based on the detected and normalized acoustic signals. The analyte concentration may be total hemoglobin (THb), oxyhemoglobin, and/or deoxyhemoglobin, for example. Steps 210, 220, and 250 may be carried out as described in U.S. patent application Ser. No. 14/793,969 filed Jul. 8, 2015 (now U.S. Pat. No. 9,380,967), Ser. No. 14/794,022 filed Jul. 8, 2015 (now U.S. Pat. No. 10,307,088), Ser. No. 14/794,037 filed Jul. 8, 2015 (now U.S. Pat. No. 10,231,656), and Ser. No. 16/253,678 filed Jan. 22, 2019, which are incorporated herein by reference.

An example of normalizing the measurement for optical energies is as follows. The first optical pulse may be at certain wavelength and having an energy E1. The first optical pulse may enter tissue and produce an acoustic response from the tissue that may be detected as a waveform S1(t), where t is time, usually on microsecond scale. The processor may be instructed to divide S1(t) by E1. The second optical pulse at the same wavelength and having an energy E2 may enter the tissue and produce an acoustic response that may be detected as a waveform S2(t), where t is time, usually on microsecond scale. The processor may be further instructed to divides S2(t) by E2. The processor may further be instructed to average these two energy-normalized waveforms (e.g., $[S1(t)/E1+S2(t)/E2]/2$) and use the average for calculating the required parameter, i.e., find the amplitude of the characteristic peak in the averaged waveform. Usually, much more than two waveforms are averaged to increase the accuracy of the calculation.

Although the above steps show method 200 of performing an optoacoustic measurement in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial or advantageous.

One or more of the steps of the method 200 may be performed with various circuitry, as described herein, for example one or more of a processor, controller, or circuit board and the like. Such circuitry may be programmed to provide one or more steps of the method 200, and the program may comprise program instructions stored on a computer readable memory or programmed steps of the logic circuitry such as programmable array logic or a field programmable gate array, for example.

EXPERIMENTAL DATA

The following data were obtained in an experiment with a phantom of a blood vessel (e.g., sheep blood within a plastic tube with 3 mm diameter, where the tube was immersed in an Intralipid solution imitating soft tissue around the vessel). The oxygenation of blood was changed gradually. At each oxygenation level, a blood sample was taken and its oxygenation was measured with a standard co-oximeter (e.g., the "gold standard"). Also, optoacoustic measurements were made at three pairs of wavelengths: 700 nm and 800 nm, 760 nm and 800 nm, and 1064 nm and 800 nm. For each pair of wavelengths, the oxygenation of blood was calculated using the corresponding algorithm derived from the published optical absorption spectra of oxy- and deoxyhemoglobin. (See, for example, https://omlc.org/spectra/hemoglobin/)

Figures 3A, 3B, 3C:
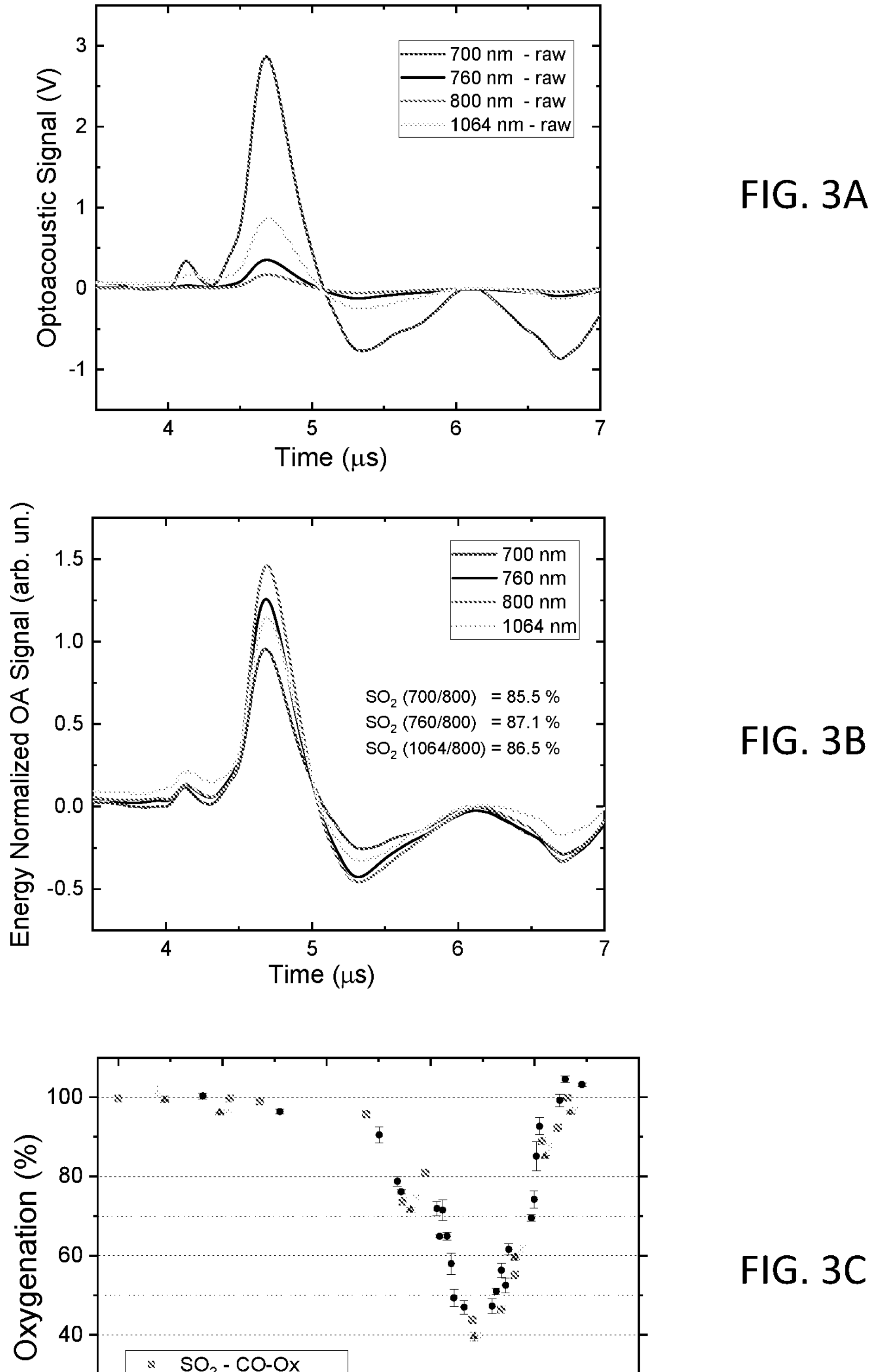
FIGS. 3A-3C show graphs of optoacoustic response in an experimental example, according to embodiments of the present disclosure.

FIG. 3A shows the averaged acoustic response (i.e., optoacoustic signal) to laser pulses at certain wavelength. The presented waveforms are not normalized for the average pulse energy at the corresponding wavelength.

FIG. 3B demonstrates the same acoustic response after normalizing the waveforms for the average pulse energy at each wavelength.

The amplitude of the most prominent peak in each waveform (i.e., peak originating from blood in the tube) is then used to calculate blood oxygenation (shown on the graph in FIG. 3B) according to the following algorithms:

For the 700/800 nm pair: $SO2=(1.17-0.5\times R1)\times 100\%$, with $R1=A(700)/A(800)$ For the 760/800 nm pair: $SO2=(1.54-0.76\times R2)\times 100\%$, with $R2=A(760)/A(800)$ For the 1064/800 nm pair: $SO2=(-0.23+1.45\times R3)\times 100\%$ with, $R3=A(1064)/A(800)$ The resulting oxygenation values for each pair of wavelengths are shown in the graph area of FIG. 3B.

FIG. 3C shows the complete set of data from that experiment. Each data point is an average of several measurements made for each pair of wavelengths (the error bars represent standard deviation). The signals from FIGS. 3A and 3B belong to the corresponding groups at around 408 minutes on the time scale in FIG. 3C.

As one can see, the blood oxygenation derived from the energy-normalized optoacoustic signals using three different algorithms correlates well with the values provided by the co-oximetry.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the inventions of the present disclosure. It is intended that the following claims define the scope of the invention and that methods and structures within the scope of these claims and their equivalents be covered thereby.

We claim:

1. A method of measuring a concentration of an analyte, the method comprising:

(a) directing a plurality of optical pulses to tissue;

(b) measuring optical energy levels of the plurality of optical pulses directed to the tissue;

(c) measuring a plurality of acoustic responses of the tissue in response to the plurality of optical pulses directed to the tissue;

(d) normalizing the plurality of measured acoustic responses based on the measured optical energy levels by forming at least one ratio of at least one of the plurality of acoustic responses to at least one corresponding measured optical energy level; and (e) determining a concentration of an analyte based on the plurality of normalized acoustic responses.

2. The method of claim 1, wherein directing the plurality of optical pulses to the tissue comprises directing a first optical pulse at a first wavelength to the tissue and directing a second optical pulse at a second wavelength to the tissue, wherein the first and second wavelengths are different.

3. The method of claim 1, wherein the plurality of optical pulses is at one or more wavelengths from 600 nm to 1,300 nm.

4. The method of claim 1, wherein the plurality of acoustic responses of the tissue are measured from a same side of the tissue the plurality of optical pulses is directed from.

5. The method of claim 1, wherein the plurality of acoustic responses of the tissue are measured from a different side of the tissue the plurality of optical pulses is directed from.

6. The method of claim 1, wherein the analyte is one or more of hemoglobin, oxyhemoglobin, and deoxyhemoglobin.

7. The method of claim 1, further comprising determining blood oxygenation based on the determined concentration of one or more analytes and the characterized property of the tissue.

8. The method of claim 1, wherein the tissue comprises one or more blood vessels and tissue surrounding the one or more blood vessels.

9. The method of claim 8, wherein the one or more blood vessels is selected from a superficial vein, a radial artery, a superior sagittal sinus, or an internal jugular vein.

10. The method of claim 1, wherein normalizing the plurality of measured acoustic responses comprises forming a ratio for each of the plurality of acoustic responses to a corresponding measured optical energy level.

11. The method of claim 10, wherein normalizing the plurality of measured acoustic responses further comprises averaging the ratios of the measured acoustic responses to the corresponding measured optical energy levels.

12. The method of claim 1, wherein the plurality of optical pulses are at a first wavelength.

13. The method of claim 12, further comprising repeating steps (a) to (d) for a plurality of optical pulses at a second wavelength different from the first wavelength.

14. The method of claim 13, wherein (e) determining the concentration of an analyte based on the plurality of normalized responses comprises determining a ratio of (i) the plurality of normalized acoustic responses to the plurality of optical pulses at the first wavelength and (ii) the plurality of normalized acoustic responses to the plurality of optical pulses at the second wavelength.

15. A system for measuring a concentration of an analyte, the system comprising:

at least one optical source configured to direct a plurality of optical pulses to tissue;

an optical energy meter configured to measure optical energy levels of the plurality of optical pulses directed to the tissue;

an acoustic detector configured to measure a plurality of acoustic responses of the tissue to the plurality of optical pulses; and a processor configured to normalize the plurality of measured acoustic responses based on the measured optical energy levels by forming at least one ratio of at least one of the plurality of acoustic responses to at least one corresponding measured optical energy level and determine a concentration of an analyte based on the plurality of normalized acoustic responses.

16. The system of claim 15, wherein the at least one optical source comprises a first optical source configured to generate a first optical pulse at a first wavelength and a second optical source configured to generate a second optical pulse at a second wavelength, wherein the first and second wavelengths are different.

17. The system of claim 15, wherein the plurality of optical pulses is at one or more wavelengths from 600 nm to 1,300 nm.

18. The system of claim 15, wherein the at least one optical source comprises a plurality of optical sources, each optical source configured to generate an optical pulse at a different wavelength.

19. The system of claim 15, wherein the at least one optical source and the acoustic detector are oriented on a same side as one another with respect to the tissue.

20. The system of claim 15, wherein the at least one optical source and the acoustic detector are oriented on different sides of one another with respect to the tissue.

21. The system of claim 15, wherein the processor is configured to normalize the plurality of measured acoustic responses by forming a ratio for each of the plurality of acoustic responses to a corresponding measured optical energy level.

22. The system of claim 21, wherein the processor is further configured to normalize the plurality of measured acoustic responses by averaging the ratios of the measured acoustic responses to the corresponding measured optical energy levels.

* * * * *